(12) United States Patent
Morgan et al.

(10) Patent No.: US 8,357,393 B2
(45) Date of Patent: Jan. 22, 2013

(54) TRANSDERMAL DELIVERY RATE CONTROL USING AMORPHOUS PHARMACEUTICAL COMPOSITIONS

(75) Inventors: Timothy Matthias Morgan, Victoria (AU); Nina Frances Wilkins, Victoria (AU); Kathryn Taci-Jane Klose, Victoria (AU); Barrie Charles Finnin, Victoria (AU); Barry Leonard Reed, Victoria (AU)

(73) Assignee: Acrux DDS Pty Ltd., West Melbourne, Victoria (AU)

( * ) Notice: Subject to any disclaimer, the term of this patent is extended or adjusted under 35 U.S.C. 154(b) by 2184 days.

(21) Appl. No.: 11/004,926

(22) Filed: Dec. 7, 2004

(65) Prior Publication Data

US 2005/0175680 A1    Aug. 11, 2005

Related U.S. Application Data

(63) Continuation of application No. PCT/AU03/00787, filed on Jun. 24, 2003.

(60) Provisional application No. 60/391,081, filed on Jun. 25, 2002.

(51) Int. Cl.
*A61K 9/12* (2006.01)
*A61K 31/568* (2006.01)

(52) U.S. Cl. ........ 424/448; 424/449; 514/872; 514/874; 514/946; 514/947

(58) Field of Classification Search .......................... None
See application file for complete search history.

(56) References Cited

U.S. PATENT DOCUMENTS

| | | | |
|---|---|---|---|
| 2,868,691 A | 1/1959 | Porush et al. | |
| 4,506,803 A * | 3/1985 | Franklin et al. | 222/1 |
| 5,082,866 A | 1/1992 | Wong et al. | |
| 5,118,494 A | 6/1992 | Schultz et al. | |
| 5,378,451 A | 1/1995 | Gorman et al. | |
| 5,962,505 A | 10/1999 | Bobrove et al. | |
| 5,968,919 A * | 10/1999 | Samour et al. | 514/177 |
| 6,004,969 A | 12/1999 | Hu | |
| 6,126,920 A | 10/2000 | Jones et al. | |
| 6,211,250 B1 * | 4/2001 | Tomlinson et al. | 514/772.4 |
| 6,231,885 B1 | 5/2001 | Carrara | |
| 6,262,057 B1 | 7/2001 | Berwaer et al. | |
| 6,299,900 B1 * | 10/2001 | Reed et al. | 424/449 |
| 6,387,383 B1 | 5/2002 | Dow et al. | |
| 6,399,093 B1 | 6/2002 | Petrus | |
| 6,432,415 B1 | 8/2002 | Osborne et al. | |
| 6,475,467 B1 | 11/2002 | Keller et al. | |
| 6,677,362 B1 | 1/2004 | Ghebre-Sellassie et al. | |
| 6,818,226 B2 * | 11/2004 | Reed et al. | 424/449 |
| 6,916,486 B2 * | 7/2005 | Klose et al. | 424/448 |
| 6,916,487 B2 * | 7/2005 | Klose et al. | 424/448 |
| 6,923,983 B2 | 8/2005 | Morgan et al. | |
| 6,929,801 B2 * | 8/2005 | Klose et al. | 424/448 |
| 6,964,777 B2 * | 11/2005 | Klose et al. | 424/448 |
| 6,998,138 B2 | 2/2006 | Chew et al. | |
| 7,094,422 B2 | 8/2006 | Chew et al. | |
| 7,387,789 B2 | 6/2008 | Klose et al. | |
| 7,438,203 B2 * | 10/2008 | Reed et al. | 222/282 |
| 2001/0005727 A1 * | 6/2001 | Stevens | 514/474 |
| 2001/0051157 A1 | 12/2001 | Breton et al. | |
| 2004/0202705 A1 | 10/2004 | Xiong et al. | |
| 2005/0002868 A1 | 1/2005 | Gonda et al. | |
| 2005/0020552 A1 | 1/2005 | Aschkenasy et al. | |
| 2005/0181032 A1 | 8/2005 | Wilkins et al. | |
| 2005/0186141 A1 | 8/2005 | Gonda et al. | |
| 2006/0280783 A1 | 12/2006 | Di Pietro et al. | |
| 2007/0071803 A1 | 3/2007 | Reed et al. | |
| 2007/0275943 A1 | 11/2007 | Morgan et al. | |
| 2008/0131494 A1 | 6/2008 | Reed et al. | |
| 2008/0152597 A1 | 6/2008 | Reed et al. | |
| 2010/0166674 A1 | 7/2010 | Morgan et al. | |
| 2010/0322884 A1 | 12/2010 | Di Pietro et al. | |

FOREIGN PATENT DOCUMENTS

| | | |
|---|---|---|
| DE | 43 34 553 A1 | 4/1995 |
| DE | 19843027 A1 * | 3/2000 |
| EP | 0 156 507 | 10/1985 |
| EP | 0 440 811 A1 | 8/1991 |
| EP | 0 581 587 A2 | 2/1994 |
| EP | 0 803 254 A1 | 10/1997 |
| GB | 1192003 | 5/1970 |
| GB | 2 137 090 A | 10/1984 |
| JP | 03/077820 | 4/1991 |
| JP | 03/083924 | 4/1991 |
| JP | 04/089423 | 3/1992 |
| WO | WO 92/06675 A1 | 4/1992 |
| WO | WO 97/29735 A | 8/1997 |
| WO | WO 97/29735 A1 | 8/1997 |
| WO | WO 9729735 A1 * | 8/1997 |
| WO | WO 99/20257 AI | 4/1999 |
| WO | WO 00/45795 A | 8/2000 |
| WO | WO 00/45795 A2 | 8/2000 |
| WO | WO 0045795 A2 * | 8/2000 |
| WO | WO 01/41755 A | 6/2001 |
| WO | WO 01/52897 A2 | 7/2001 |
| WO | WO 02/17923 A | 3/2002 |
| WO | WO 02/17927 A1 | 3/2002 |
| WO | WO 02/17967 A1 | 3/2002 |
| WO | WO 02/45687 A2 | 6/2002 |

OTHER PUBLICATIONS

Associated Press, The New York Times. "Testosterone Injections Work as Contraceptive." Apr. 3, 1996. 2 pages.*

(Continued)

*Primary Examiner* — Frederick Krass
*Assistant Examiner* — Isaac Shomer
(74) *Attorney, Agent, or Firm* — Foley & Lardner LLP

(57) ABSTRACT

A pharmaceutical composition for transdermal delivery comprising
  one or more physiologically active agents;
  one or more dermal penetration enhancers; and
  a volatile pharmaceutically acceptable carrier comprising a volatile solvent;
and wherein the physiologically active agent and dermal penetration enhancer form an amorphous deposit upon evaporation of the volatile carrier, said amorphous deposit forming a reservoir within the stratum corneum; and (A) wherein the composition has a release rate profile of physiologically active agent so as to provide a ratio of the maximum concentration ($C_{max}$) to the average concentration ($C_{avg}$) for the physiologically active agent over the dosage interval within the range of 1 to 10.

10 Claims, 13 Drawing Sheets

OTHER PUBLICATIONS

Figure 1:
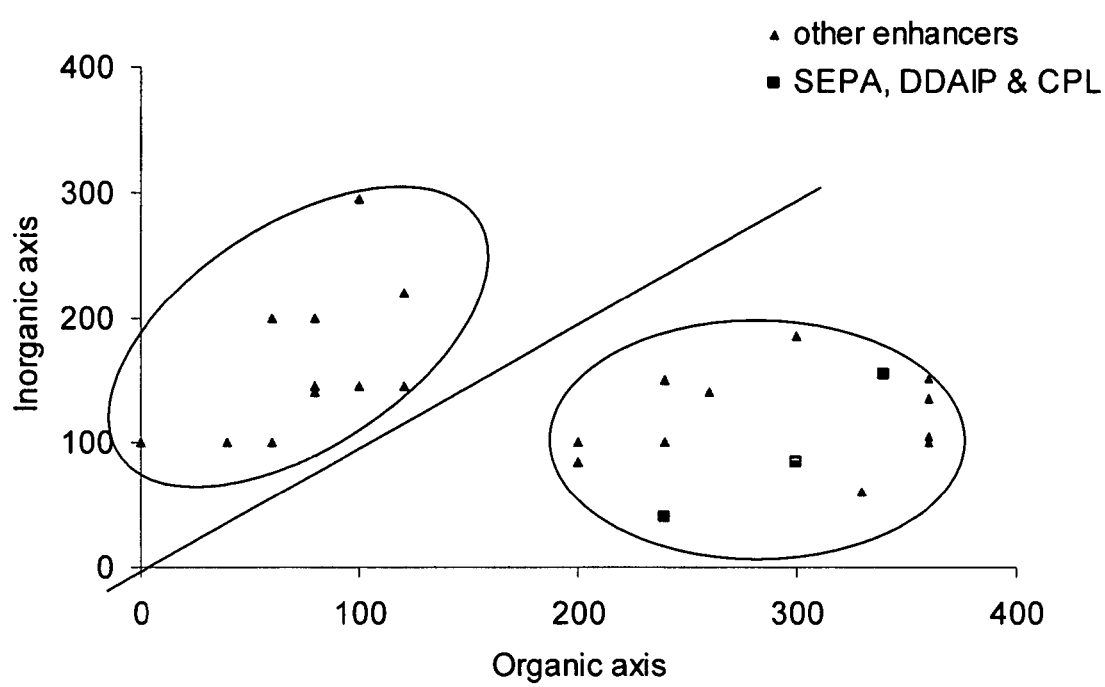

Derwent Abstract of DE 19843027 A1. 3 pages.*

Machine Translation of DE 19843027 A1 (Cordes). 4 pages. Original application published Mar. 23, 2000.*

Fraser et al., "An Initial Pharmacokinetic Study with a Metered Dose Transdermal System for Delivery of the Progestogen Nestrone as a Possible Future Contraceptive", *Contraception*, 76:432-438 (2007).

Good et al., "A New Transdermal Delivery System for Estraiol", *Journal of Controlled Release* 2:89-97 (1985).

Hilfiker, Rolf; Polymorphism: in the Pharmaceutical Industry Aug. 21, 2006, pp. 1, 21-24, 31, 33-34, 41, 259-260, 263, 269, 276, 278 and 282—accessed from http://www.mylibrary.com/Browse.asp?ID=72340&loc=Cover on Aug. 4, 2008.

Leichtnam et al., "Identification of Penetration Enhancers for Testosterone Transdermal Delivery from Spray Formulations", *Journal of Controlled Release*, 113:57-62 (2006).

Morgan, Timothy M., "Transdermal Delivery of Estradiol in Postmenopausal Women with a Novel Topical Aerosol", *Journal of Pharmaceutical Sciences*, vol. 87, No. 10, pp. 1226-1228 (1998).

Morgan, Timothy M., "Enhanced Transdermal Delivery of Sex Hormones in Swine with a Novel Topical Aerosol", *Journal of Pharmaceutical Sciences*, vol. 87, No. 10, pp. 1219-1225 (1998).

Thomas et al., "The Transdermal Revolution", *Drug Discovery Today (DDT)*, 9(16):697-703 (2004).

Vippagunta et al.., "Crystalline Solids", *Advanced Drug Delivery Reviews*, 48, pp. 3-26 (2001).

Non-Final Office Action issued Sep. 6, 2007, in U.S. Appl. No. 11/019,542 (21 pgs.).

Non-Final Office Action issued Feb. 15, 2007, in U.S. Appl. No. 11/019,542 (21 pgs.).

Non-Final Office Action issued Aug. 8, 2008, in U.S. Appl. No. 11/019,542 (14 pgs.).

Non-Final Office Action issued Mar. 9, 2009, in U.S. Appl. No. 11/019,542 (12 pgs.).

Non-Final Office Action issued Aug. 22, 2007, in U.S. Appl. No. 11/019,121 (19 pages).

Non-Final Office Action issued Sep. 17, 2007, in U.S. Appl. No. 11/019,121 (18 pages).

Non-Final Office Action issued Apr. 30, 2008, in U.S. Appl. No. 11/019,121 (21 pages).

Non-Final Office Action issued Jan. 28, 2009, in U.S. Appl. No. 11/019,121 (20 pages).

International Search Report of PCT/AU03/00784 (WO 2004/000275; U.S. Appl. No. 11/019,121).

International Search Report of PCT/AU03/00785 (WO 2004/000361; U.S. Appl. No. 11/019,542).

International Search Report of PCT/AU03/00787.

Merriam-Webster'S Collegiate Dictionary, $10^{th}$ edition, Merriam-Webster Incorporated, Springfield, Massachusetts, 1993, p. 311.

Wikipedia, "Carbon Dioxide," http://en.wikipedia.org/wiki/Cabon_dioxide, accessed Apr. 25, 2008.

Sit, "Dopamine Agonists in the Treatment of Parkinson's Disease—Past, Present and Future," *Current Pharmaceutical Design*, vol. 6, pp. 1211-1248 (2000).

Lamb et al., "Rivastigmine: A Pharmacoeconomic Review of its Use in Alzheimer's Disease," *Pharmacoeconomics*, vol. 19, No. 3, pp. 303-318 (2001).

Sundaram et al., "7α-Methyl-Nortestosterone (MENT): The Optimal Androgen for Male Contraception," *Annals of Medicine*, vol. 25, No. 2, pp. 199-205 (1993).

Lacy et al., *Drug Information Handbook*, pp. 142-143, 389-390, 762-763, 903-904, 907-908, and 1013-1014 (1999).

Office Action issued on Sep. 2, 2009, by the Examiner in U.S. Appl. No. 11/019,542 (US 2005/0181032).

Office Action issued on Dec. 18, 2008, by the Examiner in U.S. Appl. No. 11/513,342 (US 2007/0071803).

Office Action issued on Sep. 28, 2009, by the Examiner in U.S. Appl. No. 11/513,342 (US 2007/0071803).

Office Action issued on Feb. 18, 2010 by the Examiner in U.S. Appl. No. 11/019,542 (US 2005/0181032).

Office Action issued on Jun. 9, 2010 by the Examiner in U.S. Appl. No. 11/019,542 (US 2005/0181032).

Office Action issued on May 17, 2011 by the Examiner in U.S. Appl. No. 12/642,301 (US 2010/0166674).

European Search Report issued on Nov. 8, 2011 in application No. EP 10 01 0704.

Office Action issued on Jan. 18, 2012 by the Examiner in U.S. Appl. No. 12/642,301 (US 2010/0166674).

European Search Report issued on Jan. 20, 2012 for application No. EP 06741180 (corresponding to US 2006/0280783).

* cited by examiner

TRANSDERMAL DELIVERY RATE CONTROL USING AMORPHOUS PHARMACEUTICAL COMPOSITIONS

This application is a Continuation of PCT/AU03/000787 filed Jun. 24, 2003, which claims priority benefit from U.S. Provisional Application 60/391,081 filed Jun. 25, 2002.

FIELD OF THE INVENTION

The present invention relates to compositions for the transdermal delivery of physiologically active agents, to uses of those compositions, and to methods for the transdermal delivery of physiologically active agents.

BACKGROUND OF THE INVENTION

There is a constant need for methods for the safe and effective administration of physiologically active agents. For many medications it is important that the administration regime is as simple and non-invasive as possible in order to maintain a high level of compliance by a patient. Oral administration is one administration regime that is commonly used because it is a relatively simple regime to follow. However, the oral administration route is also complicated because of complications associated with gastrointestinal irritation and with drug metabolism in the liver.

Administration of physiologically active agents through the skin ('transdermal drug delivery') has received increased attention because it not only provides a relatively simple dosage regime but it also provides a relatively slow and controlled route for release of a physiologically active agent into the systemic circulation. However, transdermal drug delivery is complicated by the fact that the skin behaves as a natural barrier and therefore transport of agents through the skin is a complex mechanism.

Structurally, the skin consists of two principle parts, a relatively thin outermost layer (the 'epidermis') and a thicker inner region (the 'dermis'). The outermost layer of the epidermis (the 'stratum corneum') consists of flattened dead cells which are filled with keratin. The region between the flattened dead cells of the stratum corneum is filled with lipids which form lamellar phases that are responsible for the natural barrier properties of the skin.

For effective transdermal delivery of a physiologically active agent that is applied to the surface of the skin ('topical application'), the agent must be partitioned firstly from the vehicle into the stratum corneum, it must typically then be diffused within the stratum corneum before being partitioned from the stratum corneum to the viable epidermis, dermis and into the bloodstream.

To overcome some of the problems with transdermal delivery that are associated with transport across the dermal layers ('percutaneous absorption'), physiologically active agents can be formulated with incorporation of one or more drug penetration enhancers. For example, aqueous ethanol can be used as a vehicle in formulations for topical application. Ethanol can act as a penetration enhancer that can increase the flux of an active agent across the skin due to a solvent drag effect (Berner et al., 1989, J. Pharm. Sci, 78(5), 402-406). Padimate O, Octyl salicylate (U.S. Pat. No. 6,299,900) and Azone™ are further examples of penetration enhancers that have been shown to improve percutaneous absorption.

Compositions that form in-situ have previously found use as biodegradable in situ forming film dressings (U.S. Pat. No. 5,792,469) for the formation of barrier surfaces for open dermal wounds.

However to date the use of amorphous compositions for advanced drug delivery systems has been largely restricted to solid-state drug delivery systems such as; oral capsules an example of which is an amorphous paroxetine composition disclosed in WO 99/16440; or drug-in-adhesive, hot-melt type transdermal patches such as those disclosed in U.S. Pat. No. 5,662,923, U.S. Pat. No. 4,409,206, U.S. Pat. No. 6,264,980 and WO 95/18603. These existing amorphous delivery systems suffer from the particular disadvantage of being prone to poor stability during storage over their shelf-life which makes them particularly difficult to design and develop and in many instances has led to variability in drug release and/or dramatic changes in physical appearance (e.g. crystallization and supersaturation in drug-in-adhesive transdermal patch delivery systems). Other workers have also described the use of a transdermal spray composition that uses a film-forming composition to form a drug reservoir above the skin (U.S. Pat. No. 6,010,716) and such systems are akin to drug-in-adhesive patches that form in-situ.

Consequently there exists a need to develop new amorphous drug delivery systems with improved design and stability whilst building upon the advantages of an amorphous pharmaceutical composition.

Whilst it is feasible that transient formation of an amorphous pharmaceutical composition could occur from existing alcohol-based volatile:non-volatile vehicles such as those disclosed in a dual-phase carrier system that uses benzyl alcohol as the dermal penetration enhancer (U.S. Pat. No. 4,820,724), or those acetone-based volatile: non-volatile vehicles using DMSO, DMAC as penetration enhancers (Feldmann, R. J.; Maibach, H. I. Percutaneous penetration of 14C hydrocortisone in man. II. Effect of certain bases and pre-treatments. *Arch. Derm.* 1966, 94, 649-651). These existing volatile:non-volatile delivery systems suffer from the limitations of using water soluble dermal penetration enhancers that have poor substantivity for the skin and thus are unreliable in maintaining a stable amorphous composition within the skin over the delivery period due to their propensity to wash out of the skin. Further, these prior art systems are prone to irritate the skin due to the solvent nature of the penetration enhancers used within such prior art systems (which results in significant penetration of the enhancer into the viable epidermis).

Other methods of thermodynamic-based enhancement for improving percutaneous absorption have relied upon:
- supersaturation (Coldman, M. F.; Poulsen, B. J.; Higuchi, T. Enhancement of percutaneous absorption by the use of volatile:nonvolatile systems as vehicles. *J. Pharm. Sci.* 1969, 58, 1098-1102); or
- melting point reduction of the diffusant using deliberate selection of specific enantiomers (U.S. Pat. No. 5,114,946); or
- melting point reduction using deliberate selection of eutetic mixtures (Touitou E., Chow, D. D., Lawter, J. R. Chiral β-blockers for transdermal delivery. *Int. J. Phamm.* 1994, 104, 19-28; Kaplun-Frischoff, Y; Touitou, E. Testosterone skin permeation enhancement by menthol through formation of eutectic with drug and interaction with skin lipids. *J. Pharm. Sci.* 1997, 86, 1394-1399.; Stott, P. W., Williams, A. C., Barry, B. W. Mechanistic study into the enhanced transdermal permeation of a model β-blocker, propranolol, by fatty acids: a melting point depression effect. Int. J. Pharm. 2001, 219, 161-176.).

While these methods have all aimed at improvements in percutaneous absorption none have solved the problem of forming a stable amorphous composition capable of controlling the extent and/or profile of transdermal release of a physiologically active agent from within the skin whilst avoiding the skin irritation seen with prior art systems and compositions.

Further the benefits of a stable, in-situ forming amorphous pharmaceutical composition for release rate control within the skin are not foreseen by existing delivery systems which rely upon the control of release rate through the modification of the drug reservoir that resides above the skin such as that described for transdermal matrices that reside above the skin of the host and which are directed at deliberately modifying the profile of the transdermal drug delivery, such examples being described in U.S. Pat. No. 5,091,186 titled Biphasic transdermal drug delivery device, or U.S. Pat. No. 5,613,958, titled Transdermal delivery systems for the modulated administration of drugs or WO 93/00058, titled Solubility parameter based drug delivery system and methods for altering drug saturation concentration.

No admission is made that any reference, including any patent or patent document, cited in this specification constitutes prior art. In particular, it will be understood that, unless otherwise stated, reference to any document herein does not constitute an admission that any of these documents forms part of the common general knowledge in the art in Australia or in any other country. The discussion of the references states what their authors assert, and the applicant reserves the right to challenge the accuracy and pertinency of any of the documents cited herein.

SUMMARY OF THE INVENTION

The present invention arises from the inventor's studies of penetration enhancers and in particular from the realisation that, for finite dose formulations, any enhancement in percutaneous absorption of a physiologically active agent is likely to result from one or more of:
(a) an increase in partitioning of the agent from the vehicle containing the agent to the stratum corneum;
(b) an increase in diffusion of the agent within the stratum corneum; and
(c) an increase in partitioning of the agent from the stratum corneum to the viable epidermis.

Previous studies have indicated that the rate and extent of partitioning (a) is already quite efficient with or without added penetration enhancer (Morgan et al., 1998, J. Pharm. Sci, 87(10), 1213-1218). Other studies by the present inventors as well as others have shown that an increase in diffusivity in the stratum corneum (b) is dose dependent for the penetration enhancers studied and therefore once the maximum effect for (b) is achieved no further penetration enhancement is likely to occur.

The present invention arises, at least in part, from the realisation that an increase and/or control in the stratum corneum to viable epidermis partition coefficient (c) may be achieved by deliberately forming an amorphous drug in situ so that the drug has increased water solubility within the viable epidermis. To put the invention into practice the present inventor's have found that some combinations of physiologically active agent and penetration enhancer form an amorphous solid in situ when they are applied topically and that these combinations can be used for controlling the extent and/or profile of transdermal release of a physiologically active agent.

Accordingly, in a first form the present invention provides a composition including:
one or more physiologically active agents;
one or more dermal penetration enhancers; and
a volatile carrier comprising a pharmaceutically acceptable solvent
wherein the physiologically active agent and the dermal penetration enhancer form an amorphous deposit upon evaporation of the volatile carrier for the purpose of controlling the extent and/or profile of transdermal release of a physiologically active agent.

Amorphous deposits that are formed using compositions of the present invention can be distinguished from solid precipitate (e.g. salt derivative of a drug) or crystalline polymorphs because the amorphous deposit is formed in-situ in the skin upon evaporation of the volatile carrier. In this way, the physiologically active agent is able to rapidly partition out of the stratum corneum and into the viable epidermis. In contrast we have found that the formation of crystalline deposits in the skin typically leads to a higher propensity toward skin irritation and a decrease in percutaneous absorption efficiency (due to the need for greater energy to dissolve the crystal prior to diffusional transport). This problem increases in significance for higher melting point crystalline deposits.

Compositions of the present invention may also be more acceptable to consumers than other topical compositions because amorphous deposits have good skin feel and touch when the deposit is rubbed into the skin.

In addition to providing improved percutaneous absorption efficiency, the composition of the invention may also provide lower irritancy than some other delivery systems such as benzyl alcohol sprays, because the relatively low volume and type of volatile and non-volatile excipients used to deliver the active agent results in lower levels of irritation of the skin. Also, the composition of the present invention may avoid problems with crystallisation and/or supersaturation that are encountered with existing amorphous compositions such as amorphous type transdermal patches. This is able to be overcome because in the present invention the amorphous deposit is formed in-situ.

Accordingly in a particularly preferred embodiment the invention further provides an aerosol composition for transdermal delivery of a physiologically active agent comprising:
one or more physiologically active agents;
one or more dermal penetration enhancers; and
a volatile carrier comprising a volatile pharmaceutically acceptable solvent wherein topical application of the composition causes the physiologically active agent and dermal penetration enhancer to form an amorphous deposit on evaporation of the volatile carrier for the purpose of controlling the extent and/or profile of transdermal release of a physiologically active agent.

In a further embodiment the invention provides a pharmaceutical composition wherein the carrier comprises a hydrofluorocarbon propellant wherein topical application of the composition as an aerosol provides an amorphous deposit on evaporation of the volatile carrier, wherein the hydrofluorocarbon propellant is HFC-134a.

In a further embodiment the invention provides an aerosol applicator device for transdermal administration of physiologically active agent, the aerosol applicator comprising a chamber for containing an aerosol composition, a valve for delivering the aerosol composition and means for providing a metered dose of spray from the nozzle. The aerosol applicator may further comprise spacing means for spacing the applicator nozzle at a predetermined distance from the skin of the subject on which the spray is to be delivered.

In addition, the use of compositions of the present invention may avoid a disadvantage associated with spray nozzle blockage that is experienced with existing film-forming sprays or aerosols.

In a further aspect the present invention provides a method of delivering an amorphous drug formulation to a host, the method including the steps of applying a topical spray composition containing one or more physiologically active agents, one or more dermal penetration enhancers, and a volatile pharmaceutically acceptable solvent to the skin of the host so that the volatile solvent evaporates to form an amorphous deposit containing the active agent and the dermal penetration enhancer.

Figure 5:
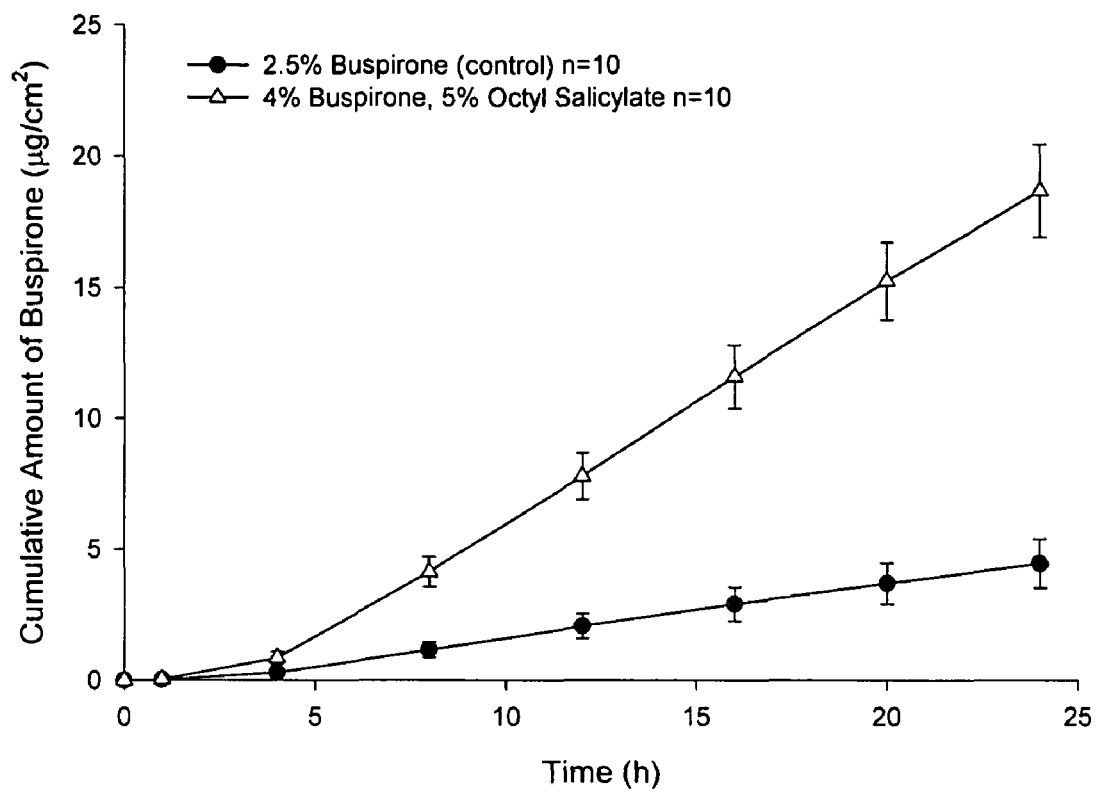
Figure 6A:
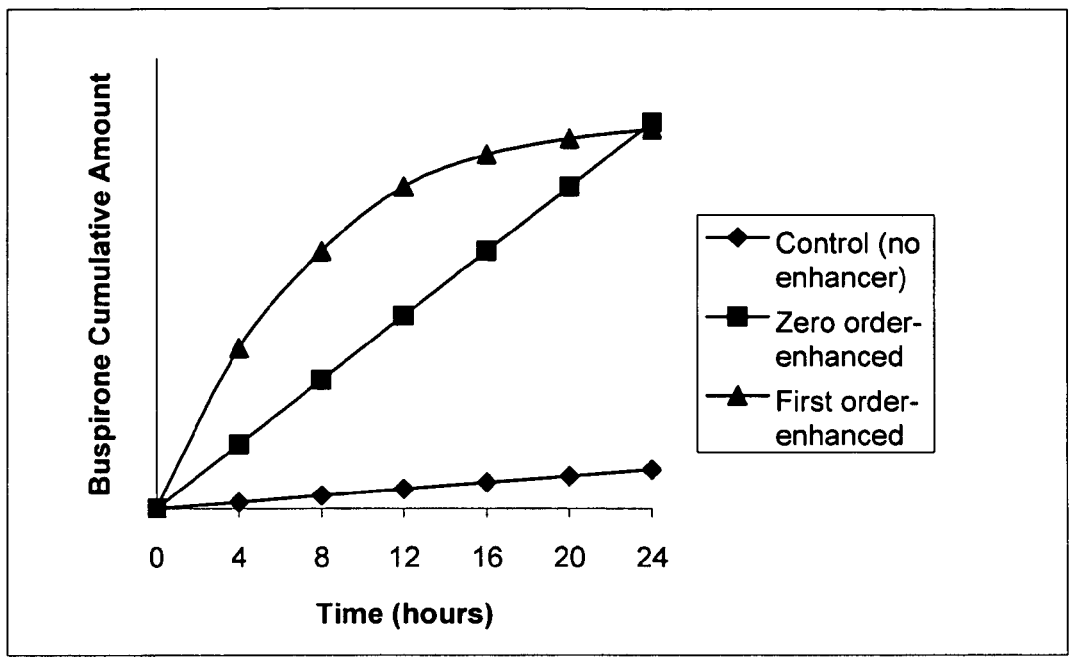
Figure 6B:
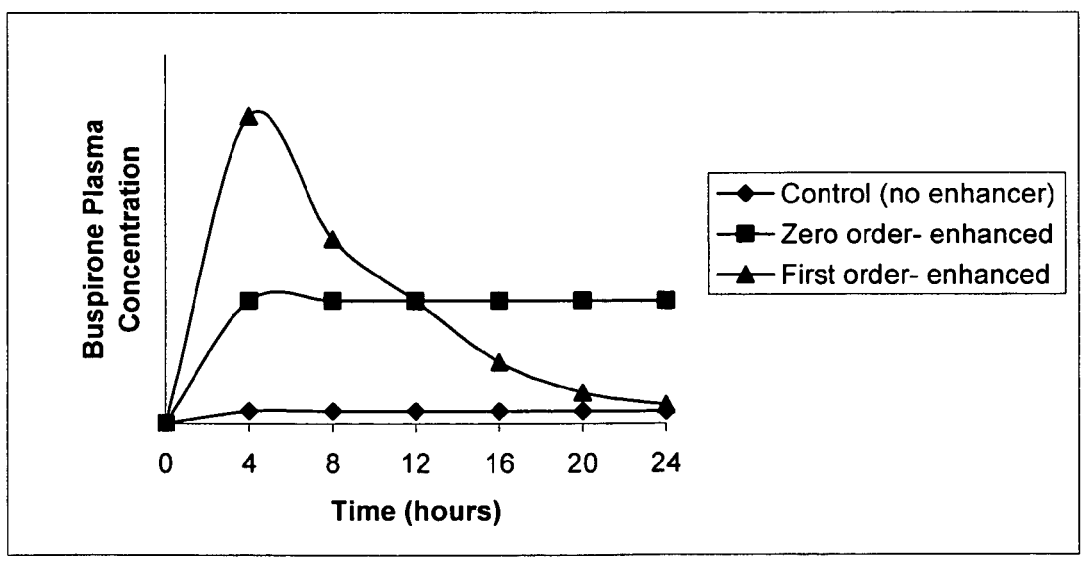
Figure 7:
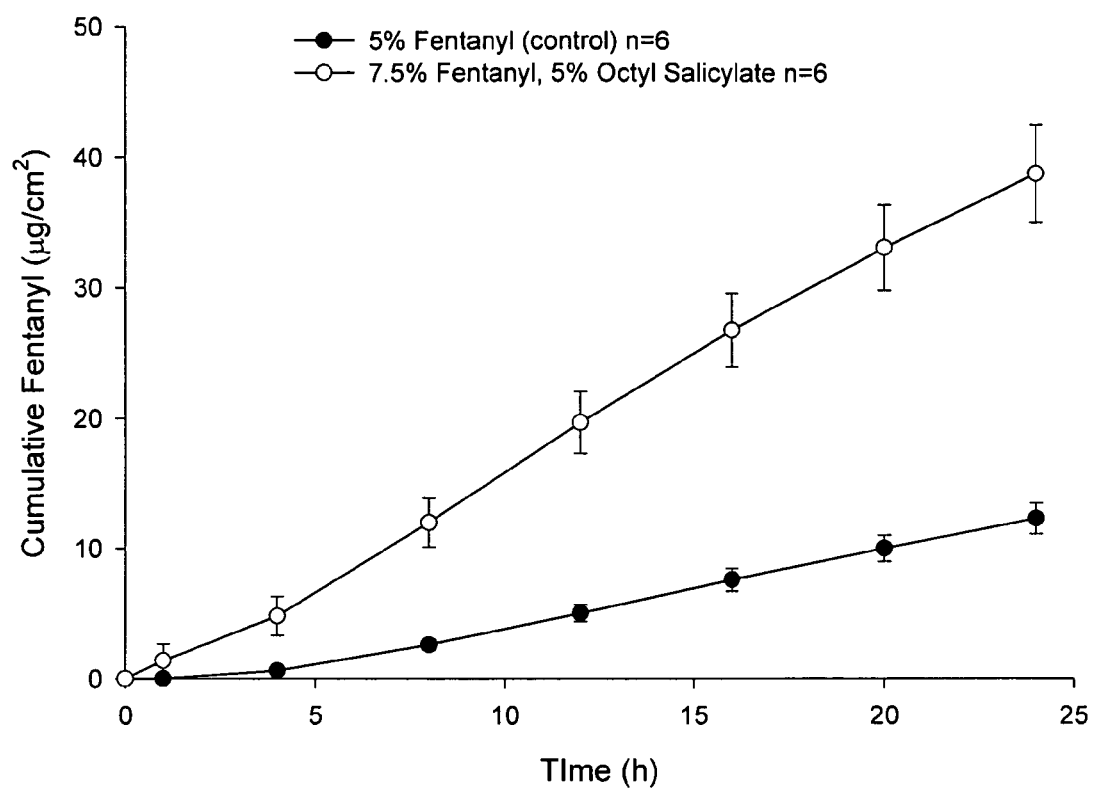
Figure 8:
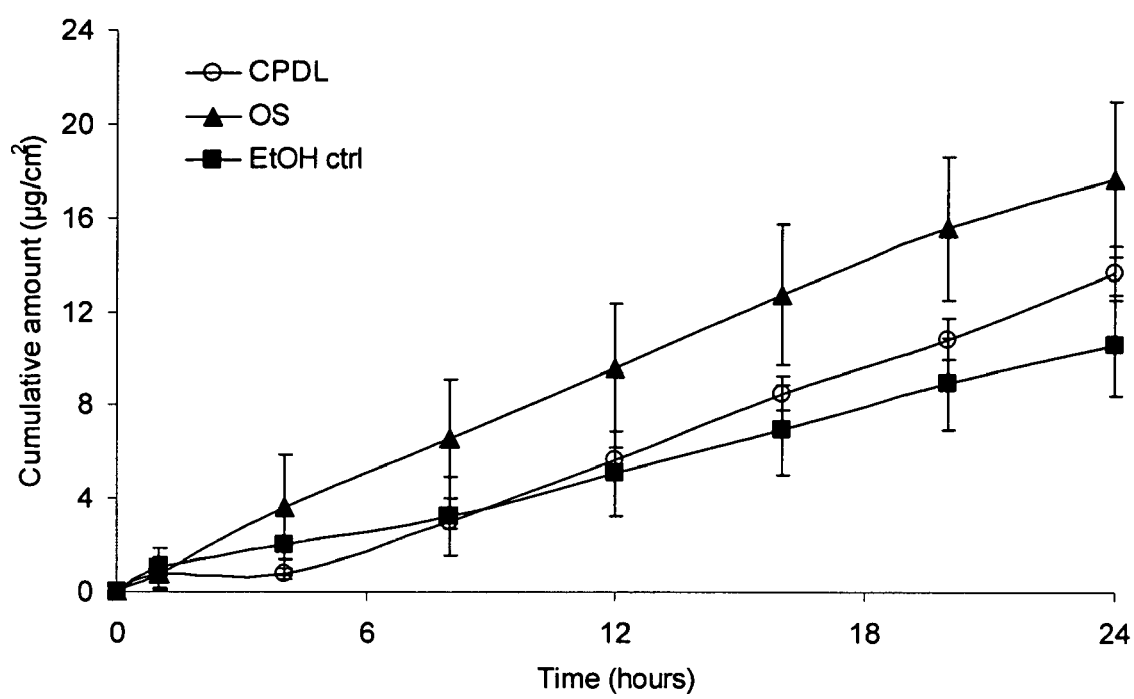

As used herein the term "amorphous" means substantially non-crystalline. It will be appreciated that, unless specified otherwise, the term amorphous includes within its scope a phase that does display some crystallinity. Amorphous for the purpose of the present invention therefore includes a phase in which only part of the deposit is in an amorphous phase. However, provided at least some of the deposit is in the amorphous phase the composition will provide the benefits of the present invention. In practice, it is preferred that at least 10% of the deposit is in the amorphous phase. The methods which may be used to assess the formation of amorphous compositions in potential compositions are Differential Scanning calorimetry (DSC) and Brightfield microscopy. We have found that these techniques, as described herein in the examples, allow the propensity of composition to form amorphous residues in-situ to be readily determined.

The combination of physiologically active agent and dermal penetration enhancer of the present invention is limited functionally to those that together form an amorphous deposit. For this reason it is preferred that both the active agent and the dermal penetration enhancer are non-volatile relative to the volatile solvent so that upon application of the composition to the skin of the host, only the volatile solvent evaporates at physiological temperatures.

In practice, it has been found that the physiologically active agent may be selected from a range of lipophilic physiologically active agents with a molecular weight less than 600 Daltons and a melting point less than 200 degrees Celcius. A list of suitable physiologically active agents includes, but is not limited to: apomorphine, butorphanol, oxybutynin, ropinirole, rivastigmine, buspirone, rizatriptin, tolterodine, zolmitriptan, lacidipine, tropisetron, olanzapine and methyl phenidate or a pharmaceutically acceptable salt or derivative of any one of the aforementioned. Most preferably, the physiologically active agent has a molecular weight less than 400 Daltons and a melting point less than 200 degrees Celcius.

In another embodiment, the suitable physiological agent is selected from the group consisting of: a steroid, a hormone derivative, an opioid analgesic, a thrombolytic, an antinauseant, an anxiolytic, an anti-migraine compound, an antihypertensive agent, an anti-malarial compound, a bronchodilator, an anti-depressant, an anti-Alzheimer's agent, a neuroleptic, an antipsychotic agent, an anti-Parkinson's agent, an anticholinergic, an antiandrogen, and an anoretic agent. In another embodiment, the suitable physiological agent is selected from the group consisting of: testosterone, oestradiol, ethinyloestradiol, nestorone, levonorgestrel, lacidipine, norethisterone acetate, buspirone, fentanyl, buprenorphine, ropinirole, scopolamine, granisetron, amlodipine, oxybutynin, rivastigmine, rizatriptan, primaquine, fluoxetine, paroxetine, tacrine, N-0923, and mazindol.

For the same reason, the dermal penetration enhancer may be selected from the classes of enhancers that are lipophilic non-volatile liquids whose vapour pressure is below 10 mm Hg at atmospheric pressure and normal skin temperature of 32 degrees Celsius. Preferably, the dermal penetration enhancer has a molecular weight within the range of 200 to 400 Daltons.

The preferred enhancers for use in accordance with the invention may be identified by their balance of organic and inorganic properties. The organic and inorganic values for each penetration enhancer for use in accordance with the invention may be determined by the method described by Fujita in "Production of organic compounds by a Conceptional Diagram" *Chem. Pharm. Bull* (Tokyo) 2:163 (1954). Whereby area 1 and area 2 possess different physicochemical properties, with area 1 being solvent based enhancers. The preferred penetration enhancers are taken from the area 2 of the conceptional diagram proposed by Hori et al *J. Pharm. Pharmacol* (1990) 42: 71-72. The preferred area spans an inorganic value of from about 0 to about 200 and an organic value of about 200 to about 400.

The preferred dermal penetration enhancers includes: fatty acids, fatty acid esters, fatty alcohols, glycols and glycol esters, 1,3-dioxolanes and 1,3-dioxanes, macrocyclic ketones containing at least 12 carbon atoms, oxazolidinones and oxazolidinone derivatives, alkyl-2-(N,N-disubstituted amino)-alkanoate esters, (N,N-disubstituted amino)-alkanol alkanoates, and mixtures thereof. Most preferably the dermal penetration enhancer is selected from the list including oleic acid, oleyl alcohol, cyclopentadecanone (CPE-218™), sorbitan monooleate, glycerol monooleate, propylene glycol monolaurate, polyethylene glycol monolaurate, 2-n-nonyl1, 3-dioxolane (SEPAT™), dodecyl 2-(N,N-dimethylamino)-propionate (DDAIP) or its salt derivatives, 2-ethylhexyl 2-ethylhexanoate, isopropyl myristate, dimethyl isosorbide, 4-decyloxazolidinon-2-one (SR-38™, TCPI, Inc.), 3-methyl-4-decyloxazolidinon-2-one, octyl salicylate (octisalate), 2-ethylhexyl 4-dimethylaminobenzoate (padimate O), Azone (1-dodecylazacyloheptan-2-one), and mixtures thereof.

Preferably the volatile solvent has a vapour pressure above 35 mm Hg at atmospheric pressure and normal skin temperature of 32 degrees Celsius. In a particularly preferred form of the invention the solvent is ethanol or isopropanol, or a mixture thereof.

The mole ratio of physiologically active agent to dermal penetration enhancer may be between 1:100 and 100:1. More preferably the mole ratio is between 1:20 and 20:1. Most preferably the mole ratio is 1:1.

Conveniently, the composition is a topical spray composition that contains the physiologically active agent, the drug penetration enhancer and the volatile solvent and the method includes the step of spraying the composition onto the skin of the host to form the amorphous deposit containing the physiologically active substance.

In each of the above cases the amorphous deposit is preferably formed in the epidermis of the host, or has a shortened residence time in the viable epidermis or dermis of the host. By 'viable epidermis' is meant the water rich tissue below the stratum corneum.

BRIEF DESCRIPTION OF THE FIGURES

In the accompanying figures:

FIG. 1 Graph showing the "Area 2" of the preferred range of inorganic and organic values of enhancers for use in compositions of the invention;

FIG. 2 DSC profiles of pure buspirone and buspirone compositions in accordance with the invention containing various penetration enhancers;

FIG. 3 Bar chart showing the melting point of a number of buspirone compositions;

FIG. 4 Graph showing the cumulative amount of buspirone diffused through human epidermis with time from a control containing buspirone and compositions containing different proportions of buspirone and 2-n-nonyl 1,3-dioxolane penetration enhancer;

FIG. 5 Graph showing the cumulative amount of buspirone diffused through human epidermis with time from a control containing buspirone and a compositions containing buspirone and octyl salicylate penetration enhancer;

FIG. 6a Graph showing the cumulative amount of buspirone diffused across skin;

FIG. 6b Graph showing the plasma concentration of buspirone after transdermal delivery according to the delivery profiles shown in 6a;

FIG. 7 Graph showing the cumulative amount of fentanyl diffused through human epidermis with time from a control containing fentanyl and a compositions containing fentanyl and octyl salicylate penetration enhancer;

FIG. 8 Graph showing the cumulative amount of fentanyl diffused through human epidermis following application of a transdermal spray composition (95% ethanol) containing fentanyl (5%) and octyl salicylate (5%, OS) penetration enhancer and a further composition containing fentanyl (5%) and cyclopentadecanolide (5%, CPDL) penetration enhancer.

Figure 9:
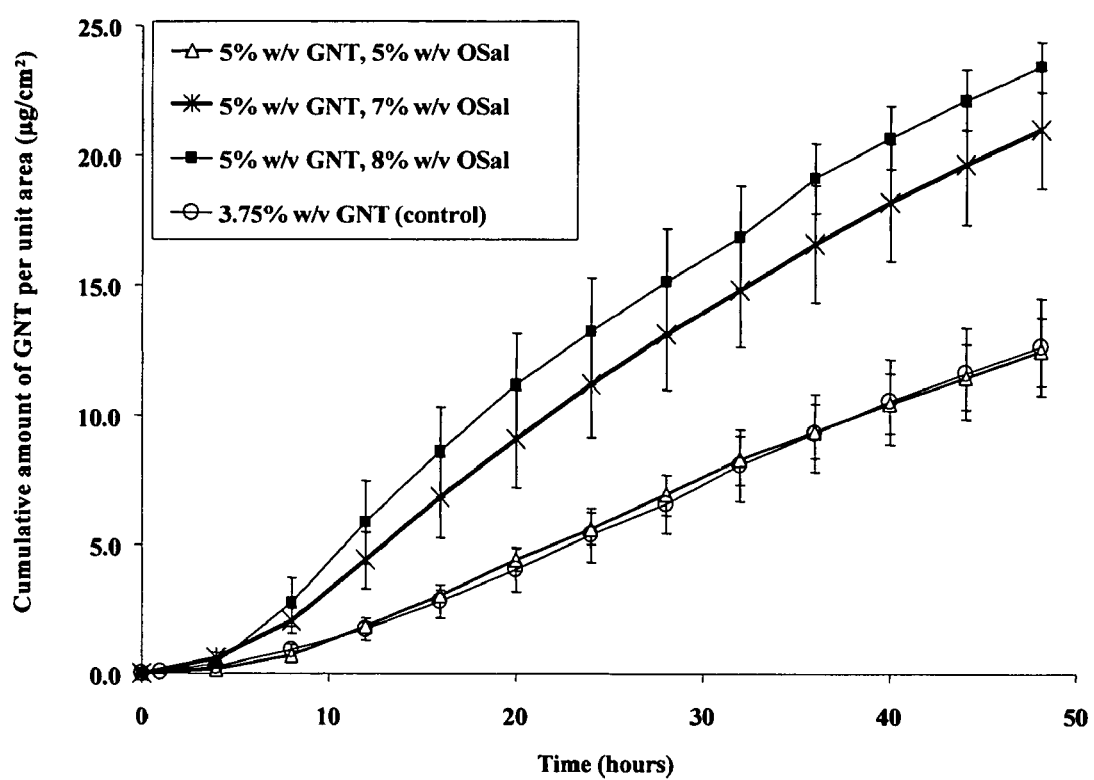

FIG. 9 Graph showing the cumulative amount of granisetron diffused through human epidermis with time from a control containing granisetron and a compositions containing granisetron and octyl salicylate penetration enhancer.

Figure 10:
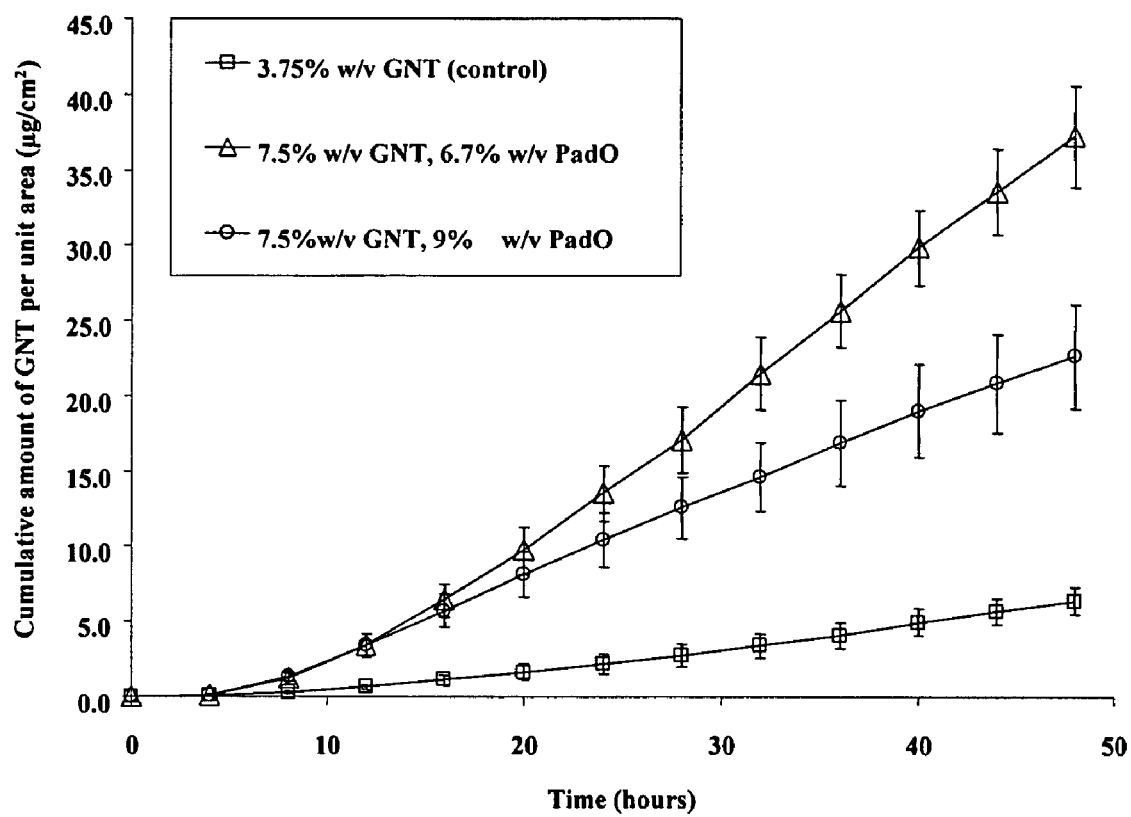

FIG. 10 Graph showing the cumulative amount of granisetron diffused through human epidermis with time from a control containing granisetron and a composition containing granisetron and padimate O penetration enhancer.

Figure 11:
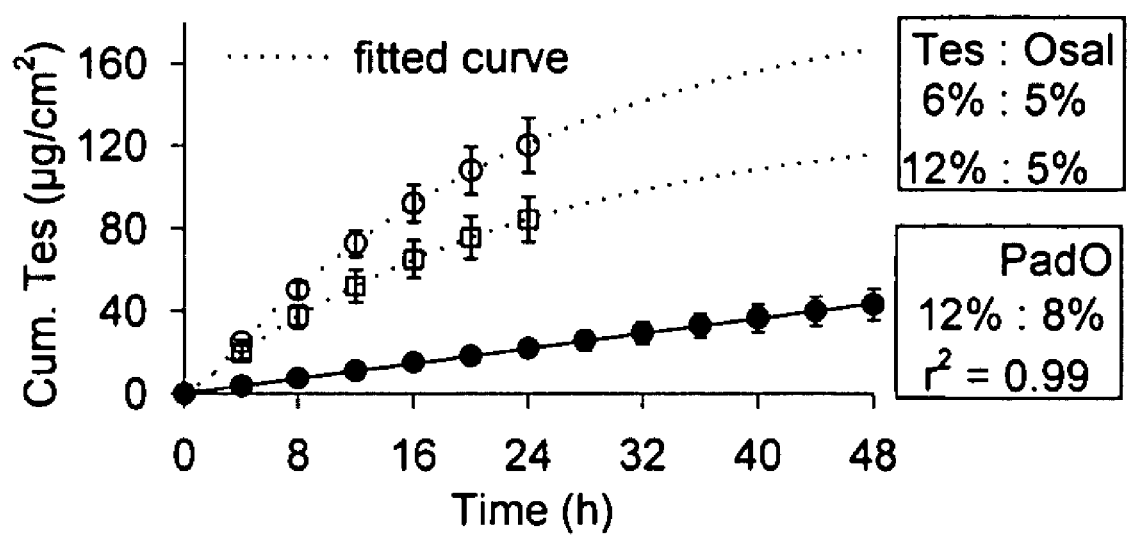
Figure 12:
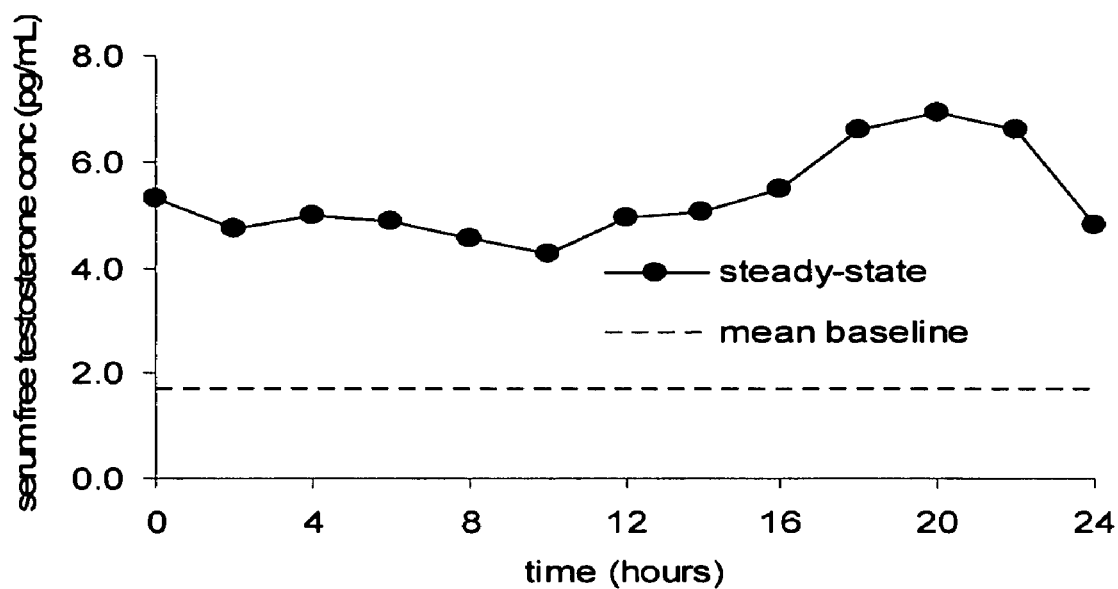

FIG. 11 Graph showing the cumulative amount of testosterone delivered with time for compositions of the invention providing a zero order or first order delivery rate using two different dermal penetration enhancers (Padimate O or Octyl salicylate);

FIG. 12 Graph showing the plasma concentrations of free testosterone in postmenopausal women at steady state from a transdermal spray composition containing octyl salicylate (ACROSS®) as the dermal penetration enhancer.

Figure 13:
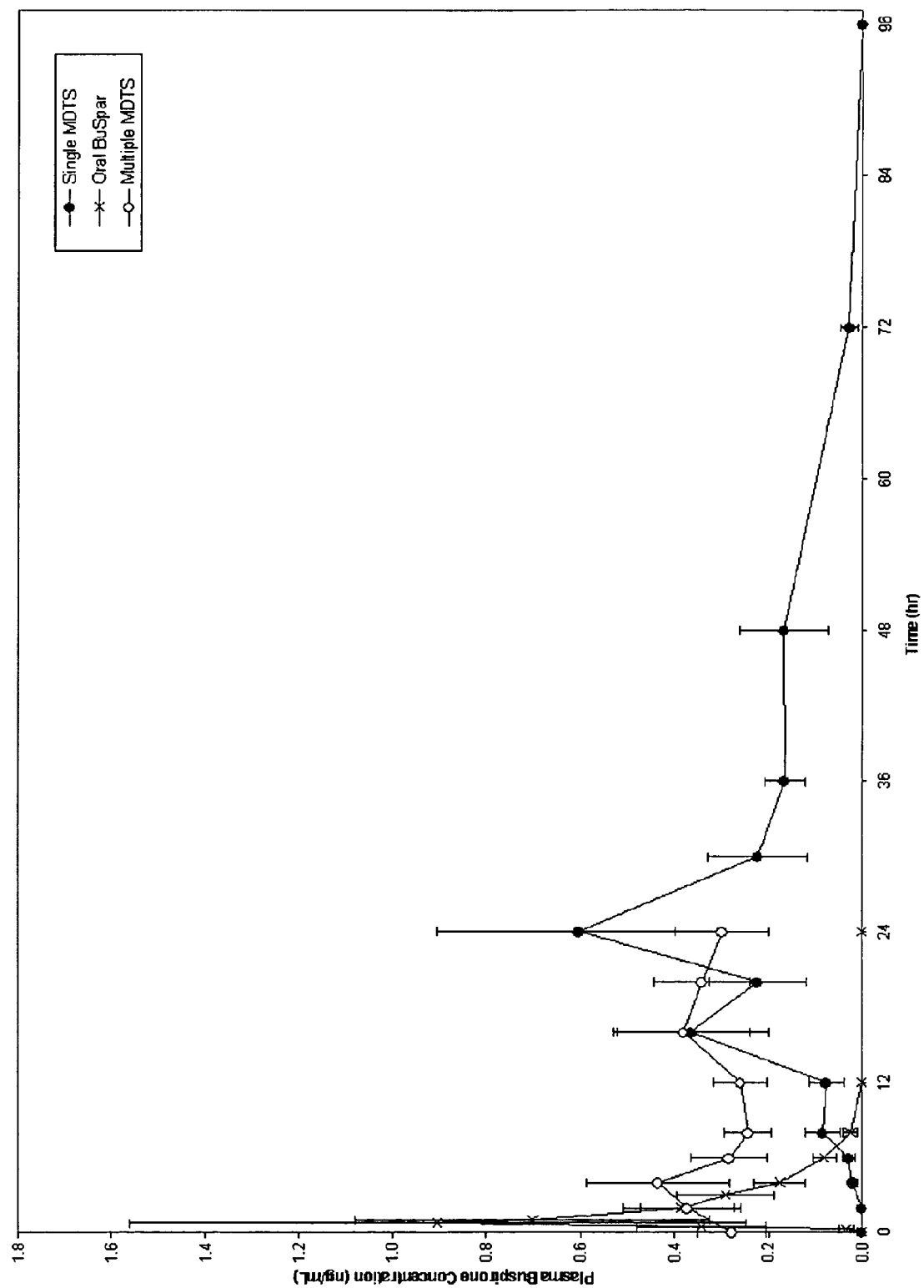

FIG. 13 Graph showing the plasma concentrations of buspirone in healthy human volunteers at steady state and from a single dose using a transdermal spray composition containing octyl salicylate (ACROSS®) as the dermal penetration enhancer; compared with a single dose of oral buspirone (Buspar) at an oral dose of 15 mg in the same subjects (crossover study design).

DETAILED DESCRIPTION OF THE INVENTION

A benefit of the present invention is that the composition is stable, which means that it is not prone to supersaturation or crystallisation during its pharmaceutical shelf life. This may be contrasted with transdermal patches in which crystallisation of the active agent has presented a problem in the past. Thus the composition of the present invention can be held in a primary container during the shelf life without encountering shelf-life problems of the prior art transdermal patches.

The composition of the present invention may contain from about 0.1% to about 10% of the physiologically active agent, from about 0.1% to about 10% of the dermal penetration enhancer, and from about 85% to about 99.8% of the volatile solvent by weight.

Preferably, the dermal penetration enhancer is non-irritating to the skin of a recipient. Thus, terpenes, benzyl alcohol and other solvent based enhancers may not be suitable for use in the compositions of the present invention because they irritate the skin by penetrating into the viable regions of the skin in appreciable quantities.

Optionally, the vehicle may have additional pharmaceutical excipients, for example gelling agents, such as carbopol and cellulose derivatives.

The release rate profile of the physiologically active agent from the amorphous deposit into the systemic circulation may be deliberately modified to adjust the delivery profile of the physiologically active agent within the systemic circulation to achieve a desired therapeutic effect.

A zero order release rate profile is achieved by forming an amorphous deposit that has a higher proportion of dermal penetration enhancer relative to the physiologically active agent and/or alternatively selecting a dermal penetration enhancer or combination of dermal penetration enhancers for which the physiologically active agent has a higher saturated solubility. In this way, the leaving tendency of the physiologically active agent from the amorphous deposit is modified and the initial burst of physiologically active agent across the skin is limited. The absolute amount of physiologically active agent can also be increased in the skin reservoir so as to reduce the extent of the plateau in the release rate profile toward the latter half of the dosage interval. The relative amount of crystalline to amorphous deposit may also be modified to achieve the desired release rate profile.

The release rate profile of the physiologically active agent from the amorphous deposit into the systemic circulation preferably approaches zero order in nature so as to reduce the ratio of maximum concentration ($C_{max}$) to the average concentration ($C_{avg}$) for the physiologically active agent over the dosage interval. In this way it is possible to reduce potential side effects associated with elevated $C_{max}$ to $C_{avg}$ ratios. For example $C_{max}$ to $C_{avg}$ ratios less than 2 and more preferably less than 1.5.

Conversely a first order release rate profile can be achieved by selecting a dermal penetration enhancer or combination of dermal penetration enhancers in which the physiologically active agent has a lower saturated solubility thus increasing the leaving tendency of the physiologically active agent from the amorphous deposit, and increasing the initial burst of physiologically active agent across the skin. The absolute amount of physiologically active agent per unit area can also be reduced in the skin reservoir so as to increase the extent of the plateau in the release rate profile toward the latter half of the dosage interval. The relative amount of crystalline to amorphous deposit may also be modified to achieve the desired release rate profile.

Preferably, the release rate profile of the physiologically active agent from the amorphous deposit into the systemic circulation is substantially first order in nature so as to increase the ratio of $C_{max}$ to $C_{avg}$ and decrease the time for maximum systemic concentration ($t_{max}$) for the physiologically active agent over the dosage interval. In this way it is possible to decrease the time to onset of therapeutic response or increase the therapeutic response after a single dose interval. For example $C_{max}$ to $C_{avg}$ ratios greater than 1.5 and more preferably greater than 2 and $t_{max}$ less than 4 to 6 hours and more preferably less than 2 to 3 hours.

The invention will now be described with reference to the following examples. It is to be understood that the examples are provided by way of illustration of the invention and that they are in no way limiting to the scope of the invention.

EXAMPLES

The method of in vitro diffusion of various physiologically active agents across human skin was used in accordance with the invention to assess the effect of addition of the various dermal penetration enhancers on transdermal drug delivery.

The methods of Differential Scanning Calorimetry (DSC) and Brightfield Microscopy were used in accordance with the invention to assess whether or not a composition is amorphous after evaporation of the volatile liquid and where necessary the extent of amorphous material present.

Diffusion Studies

In vitro diffusion experiments were performed using stainless steel flow-through diffusion cells, using human epidermis maintained at 32° C. The receptor solution consisted of either 10% Ethanol in 0.002% Sodium Azide. The non-occlusive composition was added to each of four cells at a finite dose of 5 µl per cell. Samples were collected at appropriate time points and analysed by reverse-phase high performance liquid chromatography (RP-HPLC).

a stream of nitrogen, at 10° C. per minute, within the temperature range that was drug dependent.

Brightfield Microscopy

Brightfield microscopy was used to determine the crystallisation/amorphous solid potential of various physiologically active agents in combination with a dermal penetration enhancer after volatile liquid (95% ethanol) evaporation. This enables a determination of the optimum ratio of drug to enhancer in conjunction with DSC.

5 µl aliquots of each formulation were pipetted onto a clean, glass slide at 32° C./ambient relative humidity. After evaporation of the volatile liquid vehicle (95% v/v ethanol), the slide was viewed under a Leica Wild microscope, linked to SPOT diagnostics camera, at 1 and 24 hours. The nature of

TABLE 1

HPLC conditions for receptor solution analysis.

| Parameters | Method | | |
|---|---|---|---|
| | Buspirone | Granisetron | Fentanyl |
| Column | Symmetry C18 (3.9 * 150 mm) 5 µm | Symmetry C18 (3.9 * 150 mm) 5 µm | Symmetry C18 (3.9 * 150 mm) 5 µm |
| Mobile Phase | Line A: 20% AcN in 0.01M KH2PO4 @ pH 2.85 nM Line B: 90% AcN @ pH 2.8 | 25% Acetonitrile in water with 0.14% triethylamine and 0.06% glacial acetic acid | Line A: 5 nM TEA (milli-Q), pH 10.9 Line 8: 100% AcN |
| Pump | Isocratic: 70% A 30% B | Isocratic | Gradient: Time %A %B<br>  80 20<br>8.5 63 37<br>9 80 20<br>11 80 20 |
| Flow rate | 1.0 ml/min | 1.0 ml/min | 1.0 ml/min |
| Absorbance | 239 nm | 300 nm | 210 nm |
| Injection volume | 50 µl | 50 µl | 50 µl |
| Column Temp. | 40 ° C. | — | — |

Differential Scanning Calorimetry (DSC)

DSC is used to determine changes in physicochemical properties of compounds in combination with a dermal penetration enhancer after volatile liquid evaporation. This enables determination of the optimum ratio of drug to enhancer, which results in an altered amorphous form to enhance percutaneous absorption (i.e. enhance transdermal drug delivery).

The amorphous nature of a mixture of compounds is evident in a depressed melting point of the mixture of compounds relative to the melting point of any of the individual components of the mixture. In addition, a decrease in peak height and heat of enthalpy along with a broadening of the melting transition temperature are also characteristics inherent of amorphous compounds.

Firstly, mole ratio mixtures of the physiologically active agent and dermal penetration enhancer shown were prepared in 95% ethanol as per the compositions shown. A 10 µl aluminium micro DSC pan was placed in a 50 µl DSC aluminium pan, and 5 µl aliquots of each formulation were pipetted into the 10 µl DSC pan. The volatile liquid (95% ethanol) was allowed to evaporate and further aliquots were re-applied until a sufficient quantified residue of physiologically active agent and dermal penetration enhancer remained.

The pans were maintained at ambient temperature and 33% relative humidity for 24 hours (which simulated a typical in-use daily dosage interval), after which the pans were covered and hermetically sealed. DSC was then performed under the mixture remaining after 24 hours is assessed and the proportion by volume of amorphous material may be visually estimated.

Example 1

FIG. 1 shows the organic and inorganic values for typical penetration enhancers that can be used in accordance with the invention (determined by the method described by Fujita in "Production of organic compounds by a Conceptional Diagram" Chem. Pharm. Bull, Tokyo 1954 2:163). Area 1 being solvent based dermal penetration enhancers which are prone to irritate the skin or evaporate off it when using non-occlusive percutaneous or transdermal drug delivery systems. The preferred penetration enhancers are taken from the area 2 of the conceptional diagram (as originally proposed by Hori et al J. Pharm. Pharmacol 1990 42: 71-72). The preferred area spans an inorganic value of from about 0 to about 200 and an organic value of about 200 to about 400.

Example 2

This example examines compositions of the invention formed by the combination of buspirone with a range of penetration enhancers having a range of organic and inorganic characteristics.

The physicochemical properties of buspirone are shown in the following table:

|  | M.Wt (Da) | LogP | M.Pt (° C.) |
|---|---|---|---|
| Buspirone | 385.51 | 2.63 | 103.5 |

The penetration enhancers examined in this example were 2-n-nonyl, 1,3-dioxolane (SEPA), dodecyl 2-(N,N-dimethylamino)-propionate (DDAIP) and cylclopentadecanone (CPL).

Referring to FIG. 1 there is shown a plot of inorganic index against organic index for potential penetration enhancers. The organic and inorganic values are determined according to the procedure of Fujita A *Chem. Pharm. Bull* (Tokyo) 2:173 (1954). The compounds 2-n-nonyl, 1,3-dioxolane, dodecyl 2-(N,N-dimethylamino)-propionate (DDAIP) and cyclopentadecanone demonstrate a range of organic, inorganic index in Area 2 generally defining organic index between 0 and 200 and an organic index between 200 and 400.

All formulations were prepared by accurately weighing the appropriate amount of physiological active and penetration enhancer into a volumetric flask and made up to volume with ethanol (95% v/v).
Control formulations:
Buspirone base; and
Test Formulations
All enhancer containing (test) formulations were prepared as 1:1 and 4:1 mole ratios of drug:enhancer unless stated.
Buspirone: Isopropyl myristate (IPM)
Buspirone: Dodecyl 2-(N,N-dimethylamino)-propionate (DDAIP)
Buspirone: 2-n-nonyl, 1,3-dioxolane (SEPA)
Buspirone: Laurocapram (Azone™, AZ)
Buspirone: Myristic Acid (MA)
Buspirone: 2-Ethyl Acetate (EA)

2-Ethyl Acetate (EA) which has a molecular weight of 88.1 Da and boiling point of 77.1° C. is included as an example of a solvent based dermal penetration enhancer which is not preferred for use in this invention because it is prone to irritate the skin or evaporate off it when using non-occlusive percutaneous or transdermal drug delivery systems.

Figure 2:
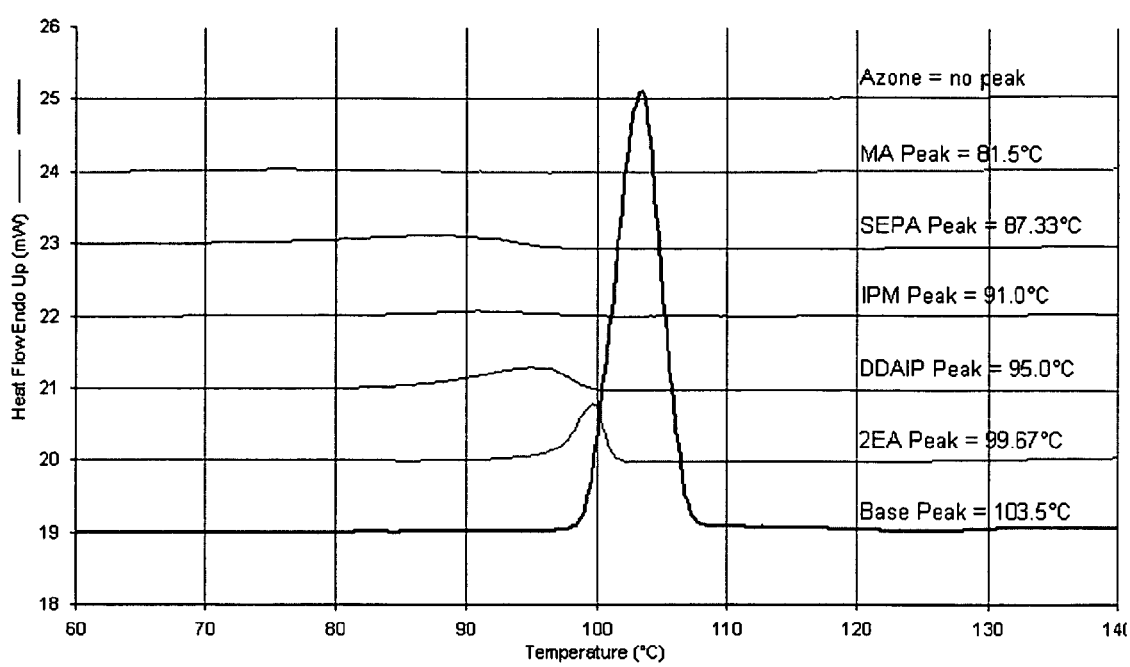

DSC profiles were determined for the control and test formulations pure buspirone and buspirone with several particular enhancers with a mole ratio of 1:1. Solvent evaporation, for each formulation, resulted in a melting point reduction. FIG. 2 demonstrates characteristics inherent of amorphous compounds, for example the decrease in melting point, ΔH and peak height, and the broadening of the melting transition temperature. DSC analysis of buspirone with each enhancer, at mole ratio of 1:1 and 4:1, showed a reduction in melting point, with buspirone:azone 1:1 ratio remaining as an oil thus presenting no melting point (FIG. 3).

Figure 3:
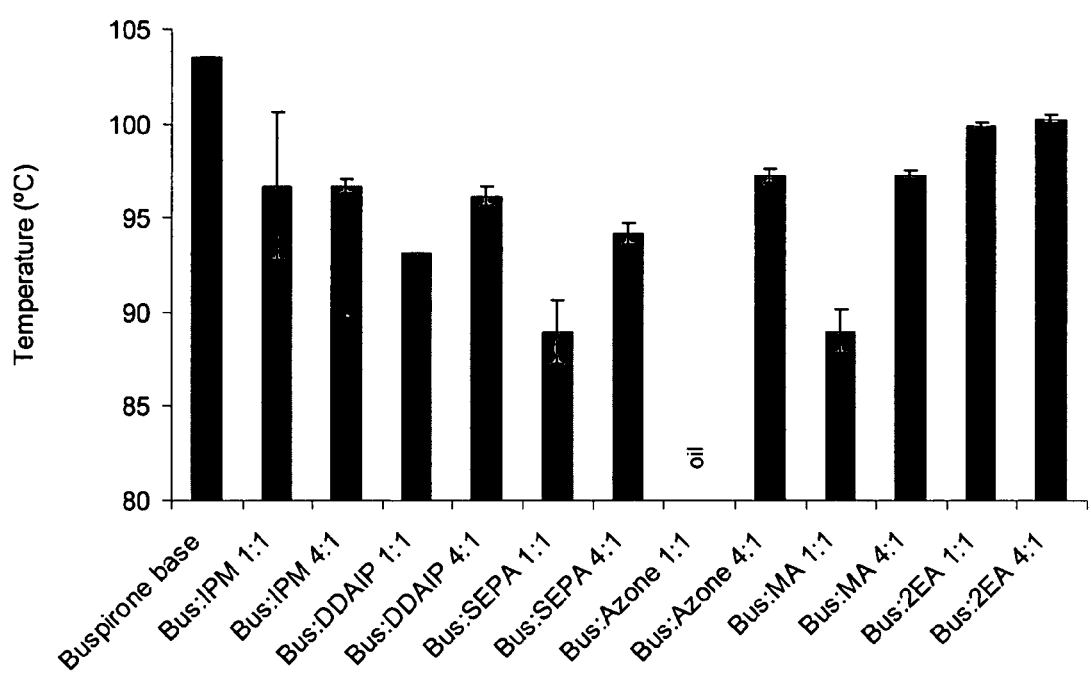

FIG. 3 also shows the inability of the solvent based enhancer (2-ethyl acetate) to reliably reduce the melting point of buspirone. This disadvantage combined with its propensity to irritate the skin is why solvent based enhancers are not preferred for the non-occlusive transdermal delivery system of this invention.

Microscopy of each binary mixture confirmed the part-amorphous state of buspirone. In most cases an unevenly spread oily film was observed, with occasional few small crystals present or some compositions with some needle shaped crystals protruding.

Figure 4:
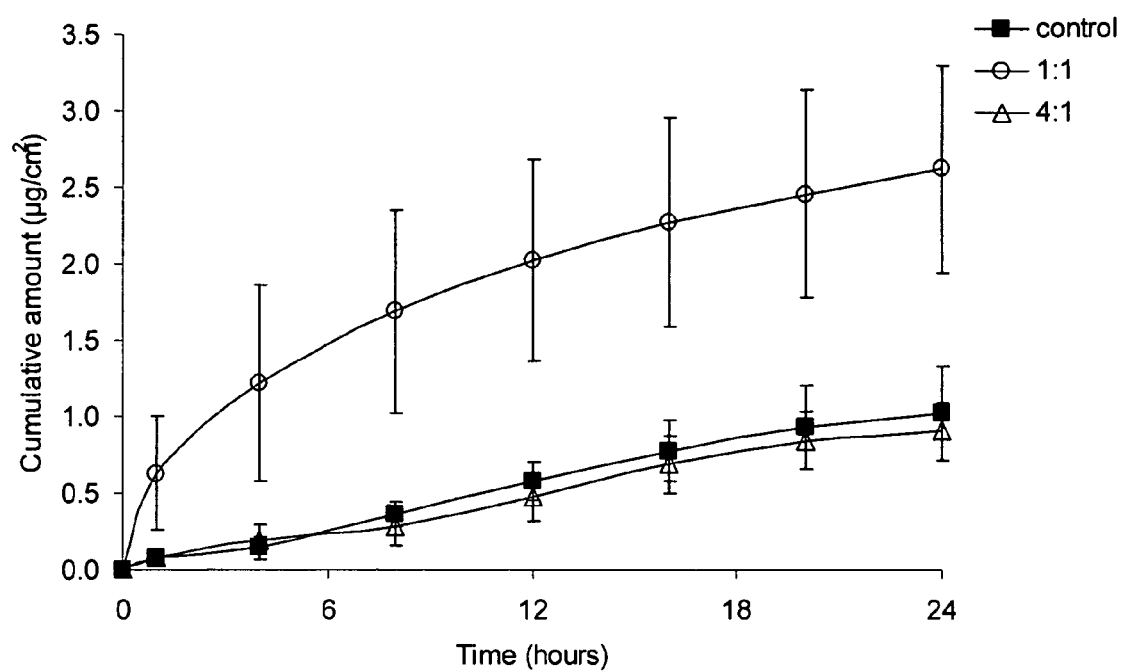

Diffusion experiments (Table 2) were performed on various 95% ethanol formulations containing buspirone and 2-n-nonyl, 1,3-dioxolane;

Buspirone diffusion through human skin (epidermis) confirms an increase in buspirone permeability at the 1:1 mole ratio with 2-n-nonyl, 1,3-dioxolane of 2.6. However, the 4:1 ratio demonstrated no significant enhancement (Table 2, FIG. 4).

TABLE 2

Summary of Mean Cumulative Amount penetrated across human epidermis at 24 hours ($Q_{24\,h}$) ($\mu g/cm^2$) for various formulations.

| Formulation (all formulations in 95% v/v Ethanol) | n | Mean $Q_{24\,h}$ Buspirone ($\mu g/cm^2$) ±SEM |
|---|---|---|
| 3.85% Buspirone in 95% EtOH | 8 | 1.028 ± 0.307 |
| 3.85% Buspirone: 2.003% 2-n-nonyl, 1,3-dioxolane (1:1 mol ratio) | 4 | 2.621 ± 0.675 |
| 3.08% Buspirone: 0.4006% 2-n-nonyl, 1,3-dioxolane (4:1 mol ratio) | 4 | 0.904 ± 0.188 |

Example 3

FIG. 5 shows the cumulative amount of buspirone diffused across human epidermis with time from a control containing buspirone in volatile liquid (95% ethanol) and a composition containing buspirone and octyl salicylate penetration enhancer in the same volatile liquid. Addition of the octyl salicylate to the transdermal spray formulation caused a significant marked increase in the amount of buspirone diffusing across the skin over 24 hours (p<0.05).

Example 4

The amorphous deposit formed in situ by the compositions of Examples 2 and 3 result in an enhanced delivery of buspirone across the skin. The delivery profile across the skin for these enhanced amorphous compositions can be either a zero order delivery profile or a first order delivery profile, whichever of these situations is desired for the particular pharmacological therapy. The composition without the enhancer shows poor penetration enhancement of buspirone across the skin and consequent low amounts of drug penetrating across the skin.

FIG. 6a depicts the diffusion profile that may be obtained by transdermal zero and first order administration of buspirone in accordance with the invention and FIG. 6b shows the approximated plasma concentration profile that would correspond to each delivery rate profile shown in FIG. 6a. The diffusion profiles of amorphous deposits investigated confirm an increase in the delivery of the active across the skin. The rate of delivery may be modified to suit the desired pharmacological therapy by either changing the dermal penetration enhancer used in the composition or by changing the ratio of drug to enhancer in the composition.

Example 5

FIGS. 7 and 8 demonstrate the ability to modify the fentanyl delivery rate by changing penetration enhancer. Therefore, the leaving tendency may be modified to suit the desired delivery rate. A stable zero order delivery rate in the case of fentanyl would be desirable for the treatment of chronic pain.

Example 6

FIGS. 9 and 10 demonstrates the ability the ability to modify the granisetron delivery rate by changing penetration enhancer and/or the ratio of drug to enhancer in the composition.

Example 7

The drug to enhancer ratio was varied to modulate the delivery rate of testosterone in vitro using transdermal spray vehicles. Varying concentrations of testosterone (Tes) and the dermal penetration enhancers octyl salicylate (Osal) or padimate O (PadO) were applied to shed snake skin in vitro from a finite vehicle volume (5 µl/cm$^2$) designed to mimic in vivo dosing. The rate and extent of drug permeation was modelled to a single compartment model with a first-order rate constant (Kubota, K. J. *Pharm. Sci.* 1991, 80, 502-504). The in vitro diffusion model allowed accurate and rapid characterisation of the diffusion profiles using three parameters alone, total % absorbed (A, units µg), rate constant (α, units h$^{-1}$) and lagtime (I, units h). Varying Tes to Osal ratio changed A and I significantly (p<0.001) and increased Tes loading in a PadO formulation resulted in zero-order delivery in vitro over 48 h as shown in FIG. 11 (suggesting the drug solubility in the enhancer plays a role in drug release). For practical formulation development purposes a simple compartmental diffusion model can be used to optimise the drug to enhancer ratio in order to modulate drug permeation across the skin.

Example 8

The plasma concentrations of free testosterone were determined in postmenopausal women at steady state from a transdermal spray composition containing testosterone 5% w/v and octyl salicylate 8% w/v in 95% ethanol. A zero-order delivery profile was obtained and is shown in FIG. 12.

Example 9

FIG. 13 shows the results for a pharmacokinetic study in 6 normal healthy male volunteers which studied a single transdermal spray dose followed by washout period; then a single oral dose of buspirone 15 mg (3×5 mg tablets; BuSpar) was given followed by washout period after which the volunteers received multiple transdermal doses once daily until steady state was achieved. The daily transdermal dosage applied was 4×91 µl sprays of the buspirone metered-dose transdermal spray (MDTS®) containing 4% w/v buspirone and 5% w/v octyl salicylate applied to the forearm.

For a single dose of the oral buspirone tablet (15 mg) the mean half-life was 2 hours and mean tmax was 0.9 hours. The mean Cavg was 0.15 ng/ml and mean Cmax was 1.3 ng/mL, with the calculated ratio of Cmax to Cavg having a value of 8.7. In contrast, following once-daily dosing of the buspirone transdermal spray of the invention the mean Cavg was 0.32 ng/ml and mean Cmax was 0.49 ng/mL, with the calculated ratio of Cmax to Cavg having a value of 1.5 and a mean t$_{max}$ of 9.3 hours. The buspirone composition of this example could be expected to have particular advantages for the use in humans or animals for the treatment of general anxiety disorders and attention deficit hyperactivity disorder whereupon the stable zero order transdermal delivery of the drug and avoidance of a high Cmax concentration provided by the invention would beneficially result in a reduction in side effects such as gastrointestinal disturbances, drowsiness, impaired driving or motor ability and/or impaired cognitive function.

The invention claimed is:

1. A non-occlusive transdermal pharmaceutical composition suitable for transdermal administration and capable of transdermal delivery of a physiologically active agent comprising:
   (a) from 0.1% to 10% by weight of one or more active agents selected from the group consisting of fentanyl, buspirone and granisetron;
   (b) from 0.1% to 10% by weight of one or more dermal penetration enhancers selected from the group consisting of octyl salicylate and Padimate O; and
   (c) from 85% to 99.8% by weight of a volatile solvent selected from the group consisting of ethanol, isopropanol, and mixtures thereof;
      wherein the combination of physiologically active agent(s) and dermal penetration enhancer(s) is such that the composition, upon application and evaporation of the solvent at physiological temperatures, forms an amorphous deposit comprising an amorphous phase, containing the dermal penetration enhancer(s) and physiologically active agent(s), which amorphous phase does not display crystallinity, when determined in vitro by Brightfield microscopy after evaporation of the solvent at 32° C. and ambient relative humidity for 24 hours.

2. A composition according to claim 1, wherein the active agent is fentanyl.

3. A composition according to claim 2, wherein the molar ratio of active agent to dermal penetration enhancer is from 1:20 to 20:1.

4. A composition according to claim 1, wherein the composition consists of the physiologically active agent(s), the penetration enhancer(s), the volatile solvent(s) and, optionally, a gelling agent.

5. A composition according to claim 1, wherein the penetration enhancer is present in an amount in the range of from 5% to 10% by weight of the composition.

6. A composition according to claim 5, wherein the active agent is fentanyl.

7. A composition according to claim 1, wherein the penetration enhancer is octyl salicylate.

8. A composition according to claim 1, wherein the composition is contained in a chamber of a spray applicator device comprising a valve for delivering the composition from the chamber, and a nozzle for dispensing the composition, wherein the spray applicator device provides a metered dose from the nozzle.

9. A non-occlusive transdermal pharmaceutical composition suitable for transdermal administration and capable of transdermal delivery of a physiologically active agent comprising:
   (a) from 0.1% to 10% by weight of the physiologically active agent fentanyl;
   (b) from 0.1% to 10% by weight of the dermal penetration enhancer octyl salicylate; and
   (c) from 85% to 99.8% by weight of a volatile solvent selected from the group consisting of ethanol, isopropanol, and mixtures thereof;
      wherein the combination of physiologically active agent and dermal penetration enhancer is such that the composition, upon application and evaporation of the solvent at physiological temperatures, forms an amorphous deposit comprising an amorphous phase, containing the dermal penetration enhancer(s) and physiologically active agent(s), which amorphous phase does not display crystallinity,
      when determined in vitro by Brightfield microscopy after evaporation of the solvent at 32° C. and ambient relative humidity for 24 hours.

10. A composition according to claim 9, wherein the composition is free of gelling agent.

* * * * *

UNITED STATES PATENT AND TRADEMARK OFFICE
CERTIFICATE OF CORRECTION

| | | |
|---|---|---|
| PATENT NO. | : 8,357,393 B2 | Page 1 of 1 |
| APPLICATION NO. | : 11/004926 | |
| DATED | : January 22, 2013 | |
| INVENTOR(S) | : Morgan et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 2,231 days.

Signed and Sealed this
Seventeenth Day of September, 2013

Teresa Stanek Rea
*Deputy Director of the United States Patent and Trademark Office*